(12) United States Patent
Rawal

(10) Patent No.: US 6,586,662 B2
(45) Date of Patent: Jul. 1, 2003

(54) YELLOW, DETERMINATE TOMATOES SUITABLE FOR PROCESSING

(75) Inventor: Kanti M. Rawal, San Leandro, CA (US)

(73) Assignee: California Hybrids, San Leandro, CA (US)

( * ) Notice: Subject to any disclaimer, the term of this patent is extended or adjusted under 35 U.S.C. 154(b) by 0 days.

(21) Appl. No.: 09/880,992

(22) Filed: Jun. 13, 2001

(65) Prior Publication Data

US 2002/0194653 A1 Dec. 19, 2002

(51) Int. Cl.$^7$ ............................ A01H 1/00; A01H 1/04; A01H 5/00; A01H 5/10; A01H 5/08
(52) U.S. Cl. .................... 800/317.4; 800/260; 800/263; 800/266; 435/411
(58) Field of Search ................................ 800/260, 263, 800/317, 317.4, 266; 435/411

(56) References Cited

U.S. PATENT DOCUMENTS 5,523,520 A * 6/1996 Hunsperger et al. ........ 435/410
6,143,960 A * 11/2000 Morrison et al. ........ 800/317.4

OTHER PUBLICATIONS

Bennett et al. 1995. Exotic germ plasm or engineered genes. pp. 88–99. (Ed. Engel, KH, Takeoka, GR, and Teranishi, R) In: Genetically modified foods. Safety Issues. Am. Chem. Soc. Symp vol. 605, ACS, Washington, DC.*

Bernacchi et al. 1998. Advanced backcross QTL analysis of tomato. II. Evaluation of near isogenic lines carrying single ddonor introgressions for desirable wild QTL alleles derived from *Lycopersicon esculentum* and *L. pimpinllifolium*. Thero Appl. genet. 97:.* do Rogo et al. 1999. Inheritance of fruit color and pigment changes in a yellow tomato (*Lycopersicon esculentum*) mutant. Genetics and Molecular Biology 22(1):101–104.*

Johjima et al. 1993. Determination of cis and trans carotenes of tangerine and yellowish tangerine tomatoes by micro thin–layer chromatography. J. Japan Soc. Hort Sci. 62(3):567–574.*

Rick et al. 1979. Chapter 53: Biosystematics studies in Lycopersicon and closely related species of Solanum. pp 667–679, In: The biology and taxonomy of the Solanaceae. Linnean Society Symp. Series No. 7, academic Press, NY.*

Eshed et al. 1996, Less–than–additive epistatic interactions of quantitative trait loci in tomato. Genetics 143:1807–1817.*

Kraft et al. 2000. Linkage disequilibrium and fingerprinting in sugar beet. Theor. Appl. Genet. 101;323–326.*

Skrdla et al. 1968. Horticultural characters and the reaction of two diseases of the world collection of the genus Lycopersicon. North Central Regional Research Publication 172. Ohio Agric. Res. and Dev. Center, Wooster, Ohio. 24 pp.*

Barton, D. W. et al., "Rules for nomenclature in tomato genetics," J. Hered., 1955, pp. 22–26, vol. 46.

Clayberg, C.D. et al., "Second list of known genes in the tomato: Including supplementary rules for nomenclature," J. Hered., Jul.–Aug. 1960, pp. 167–174, vol. 51(4).

Gould, W.A., *Tomato Production, Processing and Quality Evaluation*, Chapters 2–3, (1974), Avi Publishing Company, Inc., Westport, Connecticut.

Lamb, Frank C., *Tomato Products*, (5$^{th}$ ed. 1977), Research Laboratories, Berkeley, California.

Skrdla, W.H. et al., "Horticultural characters and reaction to two diseases of the world collection of the genus lycopersicon," North Central Regional Research Publication 172, Apr. 1968, Ohio Agricultural Research and Development Center, Wooster, Ohio.

* cited by examiner

*Primary Examiner*—David T. Fox
(74) *Attorney, Agent, or Firm*—Townsend and Townsend and Crew LLP

(57) ABSTRACT

The present invention provides yellow tomato plants producing fruit suitable for processing.

11 Claims, No Drawings

YELLOW, DETERMINATE TOMATOES SUITABLE FOR PROCESSING

BACKGROUND OF THE INVENTION

Agricultural Production:

Yellow tomatoes are commonly grown by home gardeners for their unique appearance and less acidic, sweet taste. The tomatoes harvested from such seed sources are very tender and soft. The plants are generally indeterminate in growth habit with staggered fruit set.

More than 95% of tomatoes for processing in the U.S. are grown in California. The planting begins in January in the southern part of San Joaquin Valley and continues until late May in the northern parts of the San Joaquin Valley. Most of the planting takes place by direct seeding. Less than 15% of the total acreage for processing tomatoes is transplanted with the seedlings grown in the greenhouses.

Temperatures vary widely during planting, growing and flowering time periods. For example, tomato seeds are sown in Bakersfield area in January when the daytime temperature could range 45–60° F. and nights are often below 32° F. These seeds emerge, grow, flower and set fruits from mid-February to the first week in July when temperatures gradually climb to over 100° F. in daytime and 65–75° F. at night.

In the central parts of the San Joaquin valley tomato seeds are sown in March and are harvested in August. Normally, the daytime temperature ranges from 60–70° F. in March to 85–103° F. in July and August. In Stockton, Sacramento and northern areas, the seeds are sown in April-May and harvested in September. Here the daytime temperatures range from 90–100° F. throughout the entire growing season, often with drastic cooling at night. Thus, the tomato growing industry requires tomato varieties that grow, flower and set fruit in variable environmental conditions. Yellow tomatoes from other sources do not have this ability to produce commercial yields under these conditions. Most of them abort flowers, and therefore do not produce significant yields, at high temperatures.

Last year nearly 11 million tons of tomatoes were grown in California on approximately 300,000 acres, and were harvested and processed from the first week in July to the last week in September. All of these tomatoes were red in color. These tomatoes were mechanically harvested and then transported by open bed trucks in 25-ton loads to the processing plants. Average distance between the field of production and processing plant in California is 135 miles. The tomatoes have to be very firm at full maturity and free from peduncles (stems) in order not to puncture other tomatoes in the truck. These trucks wait in the open yards under blazing sun for up to 40 hours before the tomatoes get processed. Yellow tomatoes typically are too soft and tender to survive this ordeal intact. Moreover, yellow tomatoes are typically susceptible to sunburn damage.

Mechanical harvesting involves a single harvest that destroys the tomato plants. In mechanical harvesting, concentrated fruit setting ability, concentrated maturity and ability of ripe fruit to store on the plant are critical factors that determine the efficiency of machine harvest. Small plant size and short internodes with profuse flowering are contributing factors for concentrated fruit set. In addition, the fruits have to be very firm to withstand the rigors of machine harvesting. Yellow tomatoes from other sources do not have the structural components necessary for machine harvesting.

Processing in the Factory:

Tomato products are manufactured in two principal categories, peeled and concentrated. Peeling for canned tomatoes is performed by treating the tomatoes with either steam or lye (NaOH). For steam peeling, tomatoes are scalded in live steam long enough to loosen the skin. For an efficient tomato peeling operation, it is essential that the skin be completely loosened.

Chemical peeling of tomatoes is accomplished by a 11–19% solution of Caustic soda or sodium hydroxide, also called lye. A high temperature (190–210° F.) solution of caustic soda dissolves the waxy cuticular layer of the skin of tomatoes and quickly disrupts outer tissues of the fruit while leaving the inner flesh untouched.

Only tomatoes with very firm fruit walls can be subjected to high pressure steam and/or caustic soda for peeling. Tomatoes with softer tissues do not remain intact and tend to lose significant weight during the process. Tomatoes retaining stems after harvest will not allow complete separation of the skin from the fruit walls. In addition, a significant amount of tomatoes are made sliced and diced. The fruit wall structure is extremely critical for finished product quality and commercial efficiency of sliced and/or diced tomatoes.

More than 65% red tomatoes are processed into concentrated products such as puree, sauce and paste. Tomato juice is made by grinding whole tomatoes in high temperature juice to maintain pectins and other chemical constituents of tomatoes that contribute to viscosity of juice. Purees range from light to heavy with soluble solids ranging from 8–10% for light and 11.3–15% for heavy.

Paste is generally 32% soluble solids. Juice contains 4–5.5% soluble solids. Only the tomatoes having pH of 4.3 and below (measured in fresh or cooked juice) at full maturity are suitable for processing. Most yellow tomatoes have pH values higher than 4.3, which makes them poor candidates for processing.

Ketchup, Mexican salsa, pasta sauce, pizza sauce, barbecue sauce, cocktail sauce, tomato based salad dressings and other products are manufactured from paste. Color and flavor retention are absolutely essential during the concentration process starting with the juice at 5% soluble solids and reaching paste at 32% soluble solids. Reconstituted products from paste need to have tomato taste and color for consumer acceptance.

The following traits in tomato varieties are useful for transporting and processing of tomatoes. This set of traits is designated "Processing Quality Factors" (or PQFs).

1. Holding ability of the fruit on the plant, i.e., firm fruit walls and thick skin, no decay of older fruits, no germination of seeds in the older fruits, no breakdown of sugars inside the older fruits, and no fermentation within the older fruit.
2. Firmness of the fruits to withstand mechanical harvesting and transportation as well as storage under open sky conditions at 100° F. without significant breakdown and disease development.
3. Firmness of the fruits to withstand high pressure steam (e.g., 15–30 psi at 225°–250° F.) and/or application of chemicals (e.g., 11–19% NaOH at 190–210° F.) to peel the skin off the fruits.
4. Firmness of the fruits to withstand high pressure steam for cooking as whole tomatoes.
5. Firmness of the fruits to withstand cutting to make diced tomato products.
6. Firmness of the sliced and diced tomato products to withstand cooking with high pressure steam.

The prior art lacks a yellow tomato that has these traits. The present invention addresses this and other issues.

BRIEF SUMMARY OF THE INVENTION

The present invention provides for the first time, tomato plants that have yellow fruit and have an aggregation of attributes and qualities essential for mechanical harvesting and processing. In some embodiments, the plants of the invention result from a cross between first tomato line 953C4D-1 (ATTC Accession No. PTA-3447) and a second tomato plant. Products of such crosses result in tomato plants that produce red or yellow tomatoes, either of which are suitable for processing. A preferred second tomato plant (to cross to line 953C4D-1) is homozygous for the sp and the r gene. In some aspects, the second tomato plant is tomato line 9815O2B 21s1 (ATCC Accession No. PTA-3448). The invention also provides red and yellow tomato fruit suitable for processing and seed produced from such crosses.

The invention further provides methods of making a tomato plant that produces fruit suitable for processing. In some embodiments, the methods of the invention comprise crossing first tomato line 953C4D-1 (ATTC Accession No. PTA-3447) and a second tomato plant; and selecting progeny from the cross that produce yellow tomatoes suitable for processing. In some embodiments, the tomato plant produces red fruit. In some embodiments, the tomato produced yellow fruit. For example, in some aspects, the second tomato plant is homozygous for the sp and the r gene. In some aspects, the second tomato plant is tomato line 9815O2B 21s1(ATCC Accession No. PTA-3448).

DEFINITIONS

As used herein, the phrase "suitable for processing" refers to tomato fruit having the Processing Quality Factors (or PQFs) listed above.

A plant "resulting from a cross" refers to the F1 progeny of the cross or any subsequent selfed generations of the F1 progeny (e.g., F2, F3, F4, etc.) or progeny from a backcross or test cross of the F1 progeny with a second tomato line. A plant resulting from a cross also includes plants from in vitro culture of tissue from any of the progeny discussed above, using standard tissue culture and plant regeneration techniques.

The "F1 generation" refers to the direct progeny of a cross between two tomato parent lines. An "F2 generation" refers to the direct progeny resulting from the self-pollination of an F1 plant.

A "yellow tomato" refers to a tomato with yellow ripe flesh and clear skin.

The term "determinate habit" is used herein to refer to growth of tomato varieties that have two or fewer nodes between inflorescences. Plants having a determinate habit can be distinguished from indeterminate types, which have three or more nodes between each inflorescence (see, e.g., Tigchelaar & Stevens, *Plant Breeding Reviews* 4:273–311 (1986)).

DETAILED DESCRIPTION OF THE INVENTION

The present invention provides for the first time, tomato plants that have fruit that is yellow and suitable for processing. Such plants can be produced through conventional breeding techniques. For example, at least one parent tomato lines will typically have a determinant growth habit and yellow fruit. Moreover, at least one parent will have some, and preferably all of the "processing quality factors" listed above. A preferred tomato line with all of these features is 953C4D-1 (ATTC Accession No. PTA-3447).

In addition, in some preferred embodiments, the tomato plants of the invention also have a determinate growth habit and the ability to set fruit under hot, dry conditions such as those found in California or regions with similar climates. Moreover, for yellow tomatoes, it is preferred that the fruit have the following qualities ("color qualtities") during processing:

1. Shelf stability of canned products so that the yellowness of the tomatoes does not leak into the red juice or other liquids.
2. Stability of the yellow pigment of the fruit throughout the system from fruit development on the plant through harvesting, transportation and processing.
3. Juice quality, i.e., stability of the color after concentration, restoration of color after dilution of the concentrated products derived from the juice.
4. Concentration, i.e., stability of fruit juice color and flavor under continuous cooking to prepare tomato sauce and paste via evaporation methods.
5. Dehydration, i.e., stability of the yellow color when the fruit, juice and paste are dried by heat or by freeze-dry method.

In addition, the invention provides for the development of additional tomato plants that produce fruit suitable for processing by crossing 953C4D-1 (ATTC Accession No. PTA-3447) with a second tomato plant. Depending on the genotype of the second tomato plant, the resulting hybrid (F1) will produce either red or yellow fruit. In addition, the second tomato plant may have a fruit shape or disease resistance or other agronomically important traits unrelated to PQFs. In some embodiments, the second tomato plant is a yellow tomato plant that produces fruit suitable for processing. Exemplary tomato plants with yellow fruit include, for example, tomato line 9815O2B 21s1 (ATCC Accession No. PTA-3448). In these embodiments, F1 progeny from the cross will have fruit suitable for processing, but will produce red fruit because they are heterozygous for r. F2 plants, however, can be selected for yellow fruit, and progeny from the F2 plants that breed true for yellow fruit will also produce fruit that is suitable for processing. Alternatively, tomato line 953C4D-1 can be crossed with a second tomato plant with red fruit to produce tomato plants with red fruit suitable for processing.

Hybrid plants are plants that are the direct (F1) progeny of genetically different parents. Hybrid tomato plants producing yellow fruit that are suitable for processing are particularly desirable because they typically can withstand greater variation in environmental conditions during growth than yellow tomatoes previously described. To produce a yellow hybrid tomato, it is preferred that both parents produce yellow fruit (i.e., they are homozygous r/r). Moreover, it is preferred that both parents have a determinant growth habit (i.e., they are homozygous sp/sp).

In some embodiments, new hybrid tomato plants that produce yellow fruit are developed. For example, two different high quality red tomato plants that produce fruit suitable for processing and that have desirable growth traits for a particular region are selected. Each plant is crossed with tomato line 953C4D-1, thereby creating two different F1 plants. Both F1 plants are selfed, their progeny (F2) are selfed and subsequent F3 or following generations are selected for plants that are homozygous r/r, i.e. breed true for yellow fruit. Hybrids are then created by crossing a homozygous line from the first cross with a homozygous line from the second cross.

Parental Line 953C4D-1

The parental line designated as 953C4D-1 (ATTC Accession No. PTA-3447) is homozygous for yellow colored fruit and contain the gene known as r. The r gene is recessive and results in tomato fruit having bright yellow skin with light yellow flesh, and lighter yellow flowers. Lycopene is not synthesized in the mature tomato fruit of r/r plants, but the tomatoes are otherwise normal. This gene is located on chromosome 3 short arm of *Lycopersicum esclentum* L. (pers.). See, e.g., Clayberg, C. C., et al., *J. Heredity* 57:189–196 (1966).

This parental line has been identified in the third phase of a recurrent selection-based population improvement program where the genetic stocks and varieties carrying r gene were intercrossed for several generations to the lines carrying characteristics required for commercial scale growing, mechanical harvesting and processing. This line has been identified in progeny row selections using modified single seed descent method in S3 stage of the selection scheme.

Parental line 953C4D-1 also contains a homozygous sp gene, which makes the growth habit of the plants determinate. Homozygous sp (sp/sp) alleles are reflected in a phenotype with determinate growth habit.

Line 953C4D-1 can be seeded directly or transplanted during the normal growing season for processing tomatoes in California. This variety flowers and sets fruit under normal, as well as high, temperature conditions of the San Joaquin Valley.

The following provides some of the traits of tomato line 953C4D-1:

Growth Habit: Determinate bush type plants with average internode length on the mainstem 2.4 inches; foliage covers the fruits so that there is little or no sunburn damage to the tomatoes.

Flowering: Racemes with 2–3 flowers with 1 or 2 leaves interspersed between the racemes.

Fruit: Yellow skin with the lighter yellow fruit wall color; 2–2.5" in length 1.25–1.5" in diameter; jointless, 2–3 locules, thick, very firm fruit wall, no cracking, seeds do not germinate in older fruits Juice: Yellow, containing soluble solids ranging from 4.1 to 5.6%.

Peelability: Excellent for both lye (NaOH) peeling, as well as by high pressure steam peeling. Fragments of peel do not remain attached at the stem end or at the stylar end of the fruits Parental Line 9815O2B 21s1

The parental line designated as 9815O2B 21s1 (ATCC Accession No. PTA-3448) is homozygous for yellow colored fruits with the gene known as r. This parental line has been identified in the fourth phase of a recurrent selection based population improvement program where the genetic stocks and varieties carrying r gene were intercrossed for several generations to the lines carrying characteristics required for commercial scale growing, mechanical harvesting and processing. This line has been identified in the progeny row selections using modified single seed descent method in S1 stage of the selection scheme.

Tomato line 9815O2B 21s1 also contains homozygous sp gene which makes the growth habit of the plants determinate. Homozygous sp (sp/sp) alleles are reflected in a phenotype with determinate growth habit.

The following provides some of the traits of the tomato line 9815O2B 21s1:

Growth Habit: Determinate bush type plants with average internode length on the main stem 3.2 inches; foliage covers the fruits so that there is little or no sunburn damage to the tomatoes.

Flowering: Racemes with 2–3 flowers with 1 or 2 leaves interspersed between the racemes.

Fruit: Yellow skin with the lighter yellow fruit wall color; 2.5–3.3" in length and 1.35–1.6" in diameter; jointless, 2–3 locules, thick, very firm fruit wall, no cracking, seeds do not germinate in older fruits.

Juice: Yellow, containing soluble solids ranging from 4.5 to 5.6%.

Hybrid 20

Hybrid 20 (ATTC Accession No. PTA-3446) is a tomato hybrid resulting from a cross between 9815O2B 21s1 as a female parent and 953C4D-1 as a male parent. This hybrid is homozygous for r and also for sp/sp, which results into determinate bush type plants with yellow tomatoes.

Growth Habit: Determinate bush type plants with average internode length on the main stem 3.0 inches; foliage covers the fruits so that there is little or no sunburn damage to the tomatoes.

Flowering: Racemes with 2–4 flowers with 1 or 2 leaves interspersed between the racemes.

Fruit: Yellow skin with the lighter yellow fruit wall color; 2.3–3." in length and 1.25–1.6" in diameter; jointless, 2–3 locules, thick, very firm fruit wall, no cracking, seeds do not germinate in older fruits.

Juice: Yellow, containing soluble solids ranging from 4.2 to 5.6%.

EXAMPLE

This Example describes the creation of a yellow tomato plant producing fruit suitable for processing.

Parent lines 953C4D-1 (ATTC Accession No. PTA-3447) and 9815O2B 21s1 (ATCC Accession No. PTA-3448) were crossed and F1 progeny seed was collected. The resulting plants, designated hybrid 20 (ATTC Accession No. PTA-3446) produces yellow fruit and has all of the processing quality factors and color qualities described above, as well as the ability to grow in hot, dry climates and have a determinate fruit set.

The above example is provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes. All deposits made with the American Type Tissue Culture described herein are governed by the Budapest Treaty. The deposits described herein were deposited in the American Type Culture Collection, 10801 University Blvd., Manassas, Va. 20110-2209 on Jun. 11, 2001.

What is claimed is:

1. A tomato plant resulting from a cross between 953C4D-1 (ATTC Accession No. PTA-3447) and a *L. esculentum* tomato plant homozygous for the sp and the r gene, wherein the tomato plant resulting from the cross produces yellow tomatoes with processing quality factors.

2. The tomato plant of claim 1, which is of the F1 generation from the cross.

3. The tomato plant of claim 1, wherein the *L. esculentum* tomato plant is tomato line 9815O2B 21s1 (ATCC Accesion No. PTA-3448).

4. A tomato plant, which is tomato plant hybrid 20 (ATTC Accession No. PTA-3446).

5. Seed from the tomato plant of claim 1, wherein a plant grown from the seed produces yellow fruit with processing quality factors.

6. Fruit from the tomato plant of claim 1.

7. A tomato plant, which is 953C4D-1 (ATTC Accession No. PTA-3447).

8. Seed from the tomato plant of claim 7.

9. Fruit from the tomato plant of claim 7.

10. A method of making a tomato plant which produces yellow tomatoes suitable for processing, the method comprising, crossing tomato line 953C4D-1 (ATTC Accession No. PTA-3447) and a *L. esculentum* tomato plant homozygous for the sp and the r gene; and selecting progeny from the cross that produce yellow tomatoes with processing quality factors.

11. The method of claim 10, wherein the *L. esculentum* tomato plant is tomato line 9815O2B 21s1 (ATCC Accession No. PTA-3448).

* * * * *